United States Patent
Van De Ven

(10) Patent No.: US 10,213,575 B2
(45) Date of Patent: Feb. 26, 2019

(54) VALVE

(71) Applicant: KONINKLIJKE PHILIPS N.V., Eindhoven (NL)

(72) Inventor: Richard Johannus Maria Van De Ven, Moergestel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 619 days.

(21) Appl. No.: 14/772,244

(22) PCT Filed: Jan. 31, 2014

(86) PCT No.: PCT/IB2014/058695
§ 371 (c)(1),
(2) Date: Sep. 2, 2015

(87) PCT Pub. No.: WO2014/135997
PCT Pub. Date: Sep. 12, 2014

(65) Prior Publication Data
US 2016/0001033 A1    Jan. 7, 2016

Related U.S. Application Data

(60) Provisional application No. 61/773,847, filed on Mar. 7, 2013.

(51) Int. Cl.
*A61M 16/20* (2006.01)
*A61M 39/22* (2006.01)
(Continued)

(52) U.S. Cl.
CPC ............ *A61M 16/20* (2013.01); *A61M 16/08* (2013.01); *A61M 16/202* (2014.02);
(Continued)

(58) Field of Classification Search
CPC .... A61M 16/20; A61M 16/202; A61M 16/08; A61M 39/223; A61M 16/0006;
(Continued)

(56) References Cited

U.S. PATENT DOCUMENTS

| 3,516,440 | A |   | 6/1970 | Whitlock |
| 3,575,211 | A | * | 4/1971 | Wagner ............... F15B 13/042 |
|           |   |   |        | 137/625.5 |

(Continued)

FOREIGN PATENT DOCUMENTS

| BE | 730026 A | 9/1969 |
| CN | 1603634 A | 4/2005 |

(Continued)

*Primary Examiner* — Andrew S Lo
(74) *Attorney, Agent, or Firm* — Michael W. Haas

(57) ABSTRACT

A valve comprises a housing in which a movable valve element having first and second valve members is disposed. A plurality of ports are disposed in the housing, and first and second seal portions are connected to the housing. At least one of the first seal portion and the first valve member is deformable such that, when only the first seal portion is in a sealed configuration with the first valve member, deformation allows the second seal portion to be brought into a sealed configuration with the second valve member, and/or at least one the second seal portion and the second valve member is deformable such that, when only the second seal portion is in a sealed configuration with the second valve member, deformation allows the first seal portion to be brought into a sealed configuration with the first valve member.

15 Claims, 11 Drawing Sheets

(51) Int. Cl.
*F16K 7/02* (2006.01)
*F16K 11/04* (2006.01)
*F16K 11/052* (2006.01)
*A61M 16/08* (2006.01)
*F16K 3/02* (2006.01)
*F16K 11/065* (2006.01)
*F16K 27/04* (2006.01)
*A61M 39/24* (2006.01)
*A61M 16/00* (2006.01)

(52) U.S. Cl.
CPC ........... *A61M 39/223* (2013.01); *F16K 3/029* (2013.01); *F16K 3/0227* (2013.01); *F16K 7/02* (2013.01); *F16K 11/04* (2013.01); *F16K 11/0525* (2013.01); *F16K 11/0655* (2013.01); *F16K 27/04* (2013.01); *A61M 16/0006* (2014.02); *A61M 16/0009* (2014.02); *A61M 16/204* (2014.02); *A61M 16/205* (2014.02); *A61M 2039/224* (2013.01); *A61M 2039/226* (2013.01); *A61M 2039/2433* (2013.01); *A61M 2205/0266* (2013.01)

(58) Field of Classification Search
CPC ........... A61M 16/0009; A61M 16/204; A61M 16/205; A61M 2039/224; A61M 2039/226; A61M 2039/2433; A61M 2205/0266; F16K 3/0227; F16K 3/029; F16K 7/02; F16K 11/04; F16K 11/0525; F16K 11/0655; F16K 27/04
USPC .................................................. 128/205.24
See application file for complete search history.

(56) References Cited

U.S. PATENT DOCUMENTS

| | | | |
|---|---|---|---|
| 3,884,266 | A | 5/1975 | Kondo |
| 4,739,796 | A | 4/1988 | Harding |
| 5,687,764 | A | 11/1997 | Tanaka |
| 6,966,340 | B2 | 11/2005 | Lee |
| 8,251,066 | B1 | 8/2012 | Ho |
| 9,452,409 | B2 * | 9/2016 | Waddell ............... B01J 19/087 |
| 2002/0051712 | A1 * | 5/2002 | Deninger ............ A61K 49/1815 417/53 |
| 2005/0247316 | A1 | 11/2005 | Orr |
| 2005/0268778 | A1 | 12/2005 | Chang |
| 2007/0144523 | A1 * | 6/2007 | Bolam ................. F16K 11/0712 128/205.24 |
| 2008/0093571 | A1 | 4/2008 | Desecki |
| 2010/0313885 | A1 * | 12/2010 | Kocinski ................ A61M 16/12 128/203.14 |
| 2011/0197889 | A1 | 8/2011 | Lahde |
| 2012/0285460 | A1 | 11/2012 | Smith |
| 2012/0312303 | A1 * | 12/2012 | Chambers ................ A62B 9/02 128/204.26 |

FOREIGN PATENT DOCUMENTS

| | | |
|---|---|---|
| CN | 101642599 A | 2/2010 |
| DE | 19914749 A1 | 12/1999 |
| DE | 10204608 A1 | 8/2004 |
| FR | 1497857 A | 10/1967 |
| FR | 2473667 A1 | 7/1981 |
| FR | 2565219 A1 | 12/1985 |
| JP | 2000167057 A | 6/2000 |
| JP | 2006141935 A | 6/2006 |
| JP | 2006271890 A | 10/2006 |
| WO | WO2005031199 A1 | 4/2005 |
| WO | WO2012031315 A1 | 3/2012 |

\* cited by examiner

VALVE

CROSS-REFERENCE TO RELATED APPLICATIONS

This patent application claims the priority benefit under 35 U.S.C. § 371 of international patent application no. PCT/IB2014/058695, filed Jan. 31, 2014, which claims the priority benefit under 35 U.S.C. § 119(e) of U.S. Provisional Application No. 61/773,847, filed on Mar. 7, 2013, the contents of which are herein incorporated by reference.

FIELD OF THE INVENTION

The invention relates to a valve and particularly, but not exclusively, to a valve for a cough assist device.

BACKGROUND OF THE INVENTION

The presence of secretions, such as mucus, in the airways can trap dirt and bacteria and, if allowed to accumulate, can cause infection. Coughing is the body's natural way of a removing mucus and other secretions from the lining of the airways, and thus reduces the risk of infection.

A cough begins with a deep breath. The glottis (the opening at the top of the voice box) closes, allowing the pressure to build up in the lungs. The respiratory muscles contract, and the glottis opens, forcing air back out of the lungs.

Muscles located in the rib cage, neck and abdomen play an important role during coughing. With many neuromuscular diseases, a loss of respiratory muscle strength results in a weakened ability to cough and an increased chance of respiratory infections. This may also result from spinal cord injuries.

Mechanical devices which simulate a natural cough are known, and are generally referred to as insufflation-exsufflation devices or cough assist devices. Such devices apply a positive pressure to the patient's lungs by gradually delivering a large volume of air during an insufflation phase. Once the lungs have been expanded (similar to a normal deep breath), the device quickly reverses the flow and applies a negative pressure to extract the air volume from the lungs, and, along with it, any secretions. Cough assist devices therefore help to make the patient's cough stronger and more effective, and thus maintains clear airways, thereby reducing the chance of recurring respiratory infections. An oscillation in pressure and flow may also be superimposed during the insufflation and/or exsufflation phases to loosen secretions in the patients airways.

The valve used in a cough assist device must be capable of supplying high flow rates (in the order of a few hundred liters per minute) and must be able to quickly switch in order to reverse the flow of air.

Typically, valve design is subject to competing characteristics and thus the chosen valve design is ordinarily a compromise between these characteristics. For example, it is usually desirable to provide good sealing against fluid leakage. However, doing so typically increases friction within the valve and thus reduces the switching speed of the valve.

The invention seeks to provide a valve design which is able to achieve appropriate sealing, without adversely effecting switching speed.

STATEMENTS OF INVENTION

In accordance with an aspect of the invention, there is provided a valve comprising: a housing; a plurality of ports disposed in the housing; a movable valve element disposed within the housing, the valve element having a first valve member and a second valve member; a first seal portion connected to the housing, the first seal portion being connected to the housing between a first pair of ports which are adjacent to one another and being configured to seal the first pair of ports from one another with the first valve member when the first seal portion is in a sealed configuration with the first valve member; a second seal portion connected to the housing, the second seal portion being connected to the housing between a second pair of ports which are adjacent to one another and being configured to seal the second pair of ports from one another with the second valve member when the second seal portion is in a sealed configuration with the second valve member; wherein: at least one of the first seal portion and the first valve member is deformable such that, when only the first seal portion is in the sealed configuration with the first valve member, deformation of the first seal portion and/or first valve member allows the second seal portion to be brought into the sealed configuration with the second valve member; and/or at least one of the second seal portion and the second valve member is deformable such that, when only the second seal portion is in the sealed configuration with the second valve member, deformation of the second seal portion and/or second valve member allows the first seal portion to be brought into the sealed configuration with the first valve member.

The valve members may be coupled to the movable valve element.

The valve may be a spool or butterfly valve.

The sealed configuration of the seal portions is where the seal portion, in conjunction with a respective valve member, seals the adjacent ports from one another. The seal portion and the valve member may seal directly against one another or may seal via an intermediate member positioned between the seal portion and the valve member.

The deformation of the valve members and the seal portions may be in response to the movement of the valve element. Therefore, the deformation of the seal portions may be in the direction of the movement of the valve element. On the other hand, the deformation of the seal portions may be in a direction which is opposite to the direction of movement of the valve element.

If the distance in the direction of movement between the first and second valve members is different from that of the first and second seal portions, deformation may allow both the first seal portion and the second seal portion to be brought into the sealed configuration.

The valve may have a first position in which the first and second seal portions are in the sealed configuration and a second position in which the first and second portions are in an unsealed configuration where the first pair of ports are not sealed from one another with the first valve member and the second pair of ports are not sealed from one another with the second valve member.

The valve may further comprise: a third seal portion connected to the housing between a third pair of ports which are adjacent to one another, the third seal portion being configured to seal the third pair of ports from one another when the third seal portion is in a sealed configuration with a respective valve member; a fourth seal portion connected to the housing between a fourth pair of ports which are adjacent to one another, the fourth seal portion being configured to seal the fourth pair of ports from one another when the fourth seal portion is in a sealed configuration with a respective valve member. The first and second seal portions may form a first pair of seal portions and the third and fourth seal portions may form a second pair of seal portions, the first and second pairs of seal portions being offset such that the third seal portion is disposed between the first and second seal portions in the direction of movement of the valve element.

The valve element may further comprise: a third valve member; and the first and second valve members may seal with the first pair of seal portions when the valve element is in a first position and the second and third valve members may seal with the second pair of seal portions when the valve element is in a second position. The third valve member may be deformable.

The first and second valve members may seal with the first pair of seal portions when the valve element is in a first position and the first and second valve members may seal with the second pair of seal portions when the valve element is in a second position.

The plurality of ports may comprise a first port, a second port, a third port, a fourth port and a fifth port; the first pair of ports comprising the first and second ports, the second pair of ports comprising the second and third ports, the third pair of ports comprising the third and fourth ports and the fourth pair of ports comprising the fourth and fifth ports.

The plurality of ports may comprise a first port, a second port, a third port and a fourth port; the first pair of ports comprising the first and second ports, the second pair of ports comprising the second and third ports, the third pair of ports comprising the third and fourth ports and the fourth pair of ports comprising the fourth and first ports.

The second port may be configured to receive a first fluid pressure, the fourth port may be configured to receive a second fluid pressure, and the third port may be configured to provide an output for the valve. When the valve element is in the first position, the second port may be fluidically coupled to the third port and thus provides the first fluid pressure to the output. When the valve element is in the second position, the fourth port may be fluidically coupled to the third port and thus provides the second fluid pressure to the output.

The first fluid pressure is a positive pressure and the second fluid pressure is a negative pressure.

When the valve element is in the first position, the fourth port may vent to atmosphere via the first and/or fifth port; and when the valve element is in the second position, the second port may vent to atmosphere via the first and/or fifth port.

The movable valve element may be rotatable or may be linearly translatable.

The seal portions may limit the movement of the valve element. In other words, the seal portions may be sized to prevent the valve members from moving past them.

The valve members may have a complementary shape to that of the housing. For example, the valve members may be disc-shaped. The shapes of two separate valve members may complement the shape of the housing. For example, the valve members may be semi-circular.

The valve element may be translated or rotated relative to the housing using a linear or rotary actuator, such as a voice coil motor. This may provide extremely quick and accurate movement of the valve element between the operating positions.

The valve members may be sized such that they do not contact the inner surface of the housing. Consequently, very little resistance is provided against the movement of the valve element until the valve members contact the seal portions. When operating in the first or second position, the actuator may move the valve element until a predetermined resistive force is offered by the seal portions. The predetermined resistive force may be set so as to ensure that the valve members are both sealed against the seal portions.

Further, since the valve members only contact the seal portions in the end positions, there is little or no wear during use of the valve. Accordingly, no wear particles are generated. This may be particularly beneficial in medical applications, allowing the air passing through the valve to be safely inhaled by a patient.

The valve members may be offset from one another in the direction of movement of the valve element.

Some or all of the seal portions may be o-rings or a portion thereof.

Some or all of the seal portions may comprise a bellows member. The bellows member may have a contracted state in which fluid communication across the bellows member is prevented and an expanded state in which fluid communication across the bellows member is permitted.

The bellows member may comprise one or more holes which are obstructed when the bellows member is in the contracted state and which are unobstructed when the bellows member is in the expanded state.

The bellows member may provide an adequate seal over a range of contracted states (the sealed range of the bellows member). In other words, the effective length of the bellows member may vary whilst maintaining an adequate seal.

Some or all of the seal portions may comprise a stretchable material. The stretchable material may prevent fluid communication through it when unstretched and may permit fluid communication through it when stretched.

The stretchable material may comprise one or more holes which increase in size as the stretchable material is stretched.

Some or all of the ports encompassed by the pairs of ports described previously may overlap with ports of other pairs. For example, where the valve comprises two ports and a rotatable valve element, the first valve member may separate a first port from a second port and the second valve member may separate the second port from the first port.

The deformation of the valve members and seal portions is able to counteract deviations in the positions of the valve members and/or the seal portions. For example, the valve members may be spaced apart from one another in the direction of movement by a distance which is different from that desired. Such deviations may result from manufacturing tolerances or thermal expansion or contraction of the components, for example. The deformation ensures that an effective seal is provided between the valve members and the seal portions.

By making the valve members deformable, for example, by making their thickness very small, the inertia of the valve element is reduced. The low inertia of the valve element is beneficial for the switching speed of the valve. Further, the force or torque required to move the valve element can be minimized, thus reducing the required switching power.

Both the seal portions and valve members may be deformable. The combined deformation of the seal portions and the valve members can counteract larger deviations in the positions of the seal portions and the valve members.

The spacing between the valve members may be configured such that an effective seal is formed between the valve members and the seal portions over the range of anticipated deviations.

In accordance with another aspect of the invention, there is provided a valve comprising: a housing; a plurality of ports disposed in the housing; a movable valve element disposed within the housing, the valve element having a first valve member and a second valve member; a first seal portion connected to the housing, the first seal portion being connected to the housing between a first pair of ports which are adjacent to one another and being configured to seal the first pair of ports from one another with the first valve member when the first seal portion is in a sealed configuration with the first valve member; a second seal portion connected to the housing, the second seal portion being connected to the housing between a second pair of ports which are adjacent to one another and being configured to seal the second pair of ports from one another with the second valve member when the second seal portion is in a sealed configuration with the second valve member; wherein: at least one of the first seal portion, the second seal port, the first valve member and the second valve member is deformable such that, when only the first seal portion is in the sealed configuration, deformation of at least one of the first seal portion, the second seal portion, the first valve member and the second valve member allows the second seal portion to be brought into the sealed configuration.

Where the second seal portion is not in the sealed configuration such that the second seal portion is spaced from the second valve member, the second seal portion and/or the second valve member may deform towards one another so as to bring the second seal portion into the sealed configuration. This may require an external influence which deflects the second seal portion and the second valve member towards one another. For example, the valve member may be formed from a shape memory alloy which when heated deforms to a different shape (i.e., its original, cold-forged shape). Accordingly, where the second seal portion is not in the sealed configuration, the second valve member may be heated such that it deforms and brings the second seal portion into the sealed configuration with the second valve member.

In accordance with another aspect of the invention, there is provided a cough assist device comprising a valve as described above.

BRIEF DESCRIPTION OF THE DRAWINGS

For a better understanding of the present disclosure, and to show more clearly how it may be carried into effect, reference will now be made, by way of example, to the accompanying drawings, in which.

DETAILED DESCRIPTION OF THE EMBODIMENTS

Figure 1:
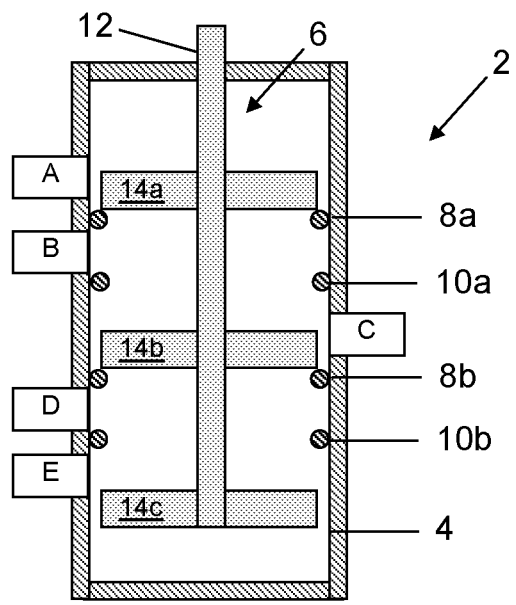
FIG. 1 is a cross-sectional view of a valve according to a first embodiment of the invention.

FIG. 1 shows a valve 2 according to a first embodiment of the invention. The valve is a directional spool-type valve.

The valve 2 comprises a housing 4 in which a movable valve element 6 is disposed.

The housing 4 defines a generally cylindrical chamber. A plurality (five are shown in FIG. 1) of ports, labeled A-E, are provided in the wall of the housing 4. The ports A-E extend through the wall of the housing 4 and open into the chamber defined by the housing 4.

A plurality of seal portions are affixed to the housing 4 within the chamber. In the present embodiment, the seal portions are O-rings or other similar types of seals. The seal portions comprise an upper pair formed by a first upper seal portion 8a and a second upper seal portion 8b, and a lower pair formed by a first lower seal portion 10a and a second lower seal portion 10b.

The first and second upper seal portions 8a, 8b are spaced from one another, as are the first and second lower seal portions 10a, 10b. The spacing between each of the first and second upper seal portions 8a, 8b and the first and second lower seal portions 10a, 10b is equal. The positions of the upper and lower pairs are offset from one another such that the upper and lower pairs are interleaved with one another. Specifically, the positions of the upper and lower pairs are offset such that the first lower seal portion 10a is disposed between the first and second upper seal portions 8a, 8b.

The positions of ports A-E will now be described with reference to the seal portions 8, 10. Port A is provided above the first upper seal portion 8a. Port B is provided between the first upper seal portion 8a and the first lower seal portion 10a. Port C is provided between the first lower seal portion 10a and the second upper seal portion 8b. Port D is provided between the second upper seal portion 8b and the second lower seal portion 10b. Port E is provided below the second lower seal portion 10b.

Although port C is shown as being diametrically opposed to ports A, B, D and E, this need not be the case. For example, ports A-E may all be located on one side of the housing or may be arranged in any combination of positions about the full circumference of the housing 4.

The movable valve element 6, which may be commonly referred to as a spool or piston, comprises a central stem 12 and a plurality of valve members (three are shown in FIG. 1), labeled 14a-14c, which are provided on the stem 12. The valve members comprise an upper valve member 14a, a central valve member 14b, and a lower valve member 14c.

The valve members 14a-14c are spaced along the stem 12 and are fixed relative to the stem 12. The valve members 14a-14c have a complementary shape to the cross-section of the chamber defined by the housing 4. Therefore, in this embodiment, the valve members 14a-14c are disc-shaped. The valve members 14a-14c are sized so that they may not pass through the seal portions 8, 10. The seal portions 8, 10 therefore act as stops which limit the movement of the valve element 6. Further, whilst the valve members 14a-14c have a complementary shape to the chamber, they are sized slightly smaller such that they do not ordinarily contact the inner surface of the wall of the housing 4.

The positions of the valve members 14a-14c will now be described with reference to the seal portions 8, 10. The upper valve member 14a is provided above the first upper seal portion 8a and is configured to seal against an upper surface of the first upper seal portion 8a. The central valve member 14b is provided between the first lower seal portion 10a and the second upper seal portion 8b and is configured to seal against either a lower surface of the first lower seal portion 10a or an upper surface of the second upper seal portion 8b. The lower valve member 14c is provided below the lower second seal portion 10b and is configured to seal against a lower surface of the second lower seal portion 10b. As described, the valve members 14a-14c seal against the upper surfaces of the upper pair of seal portions 8a, 8b and against the lower surfaces of the lower pair of seal portions 10a, 10b.

Figure 2:
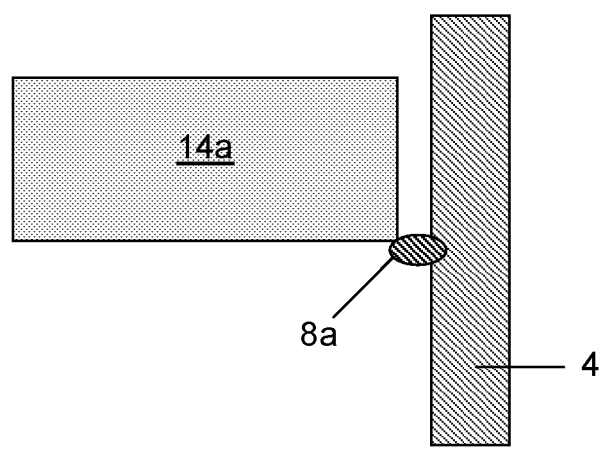
FIG. 2 is an enlarged view of a portion of the valve shown in FIG. 1.

As shown in FIG. 2, the seal portions 8, 10 are deformable under force applied by the respective valve member. This mechanism will be described further below.

The valve element 6 is translatable relative to the housing 4 so as to adjust the positions of the valve members 14a-14c. As described previously, the valve members 14a-14c are sized so that they may not pass through the seal portions 8, 10. Accordingly, the seal portions 8, 10 limit the movement of the valve element 6.

The positions of the valve element 6 will now be described with reference to the schematic illustrations provided in FIGS. 3 to 6. In FIGS. 3 to 6, ports A and E are shown as being provided at ends of the housing 4, however they may be arranged as shown in FIG. 1.

Figure 3:
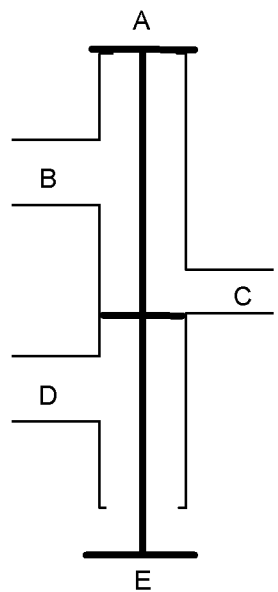
FIG. 3 is a schematic view of the valve in a first position.

FIG. 3 shows a first position of the valve element 6 in which the upper valve member 14a is sealed against the upper surface of the first upper seal portion 8a, the central valve member 14b is sealed against the upper surface of the second upper seal portion 8b, and the lower valve member 14c is spaced from the lower surface of the second lower seal portion 10b.

In the first position, ports B and C are in fluid communication with one another, and ports D and E are in fluid communication with one another.

Figure 4:
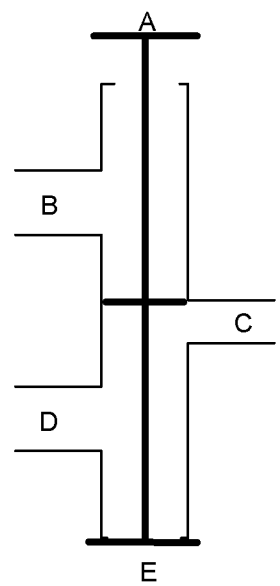
FIG. 4 is a schematic view of the valve in a second position.

FIG. 4 shows a second position of the valve element 6 in which the upper valve member 14a is spaced from the upper surface of the first upper seal portion 8a, the central valve member 14b is sealed against the lower surface of the first lower seal portion 10a, and the lower valve member 14c is sealed against the lower surface of the second lower seal portion 10b.

In the second position, ports A and B are in fluid communication with one another, and ports C and D are in fluid communication with one another.

Figure 5:
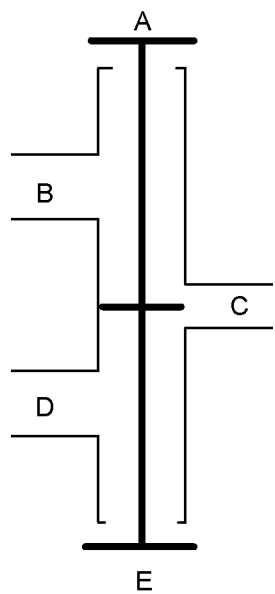
FIG. 5 is a schematic view of the valve in a third position.

FIG. 5 shows a third position of the valve element 6 which is midway between the first and second positions described previously. In the third position, the upper valve member 14a is spaced from the upper surface of the first upper seal portion 8a, the central valve member 14b is spaced from both the lower surface of the first lower seal portion 10a and the upper surface of the second upper seal portion 8b, and the lower valve member 14c is spaced from the lower surface of the second lower seal portion 10b.

In the third position, none of the valve members 14a-14c are sealed against any of the seal portions 8, 10. Consequently, ports A-E are all in fluid communication with one another.

Figure 19:
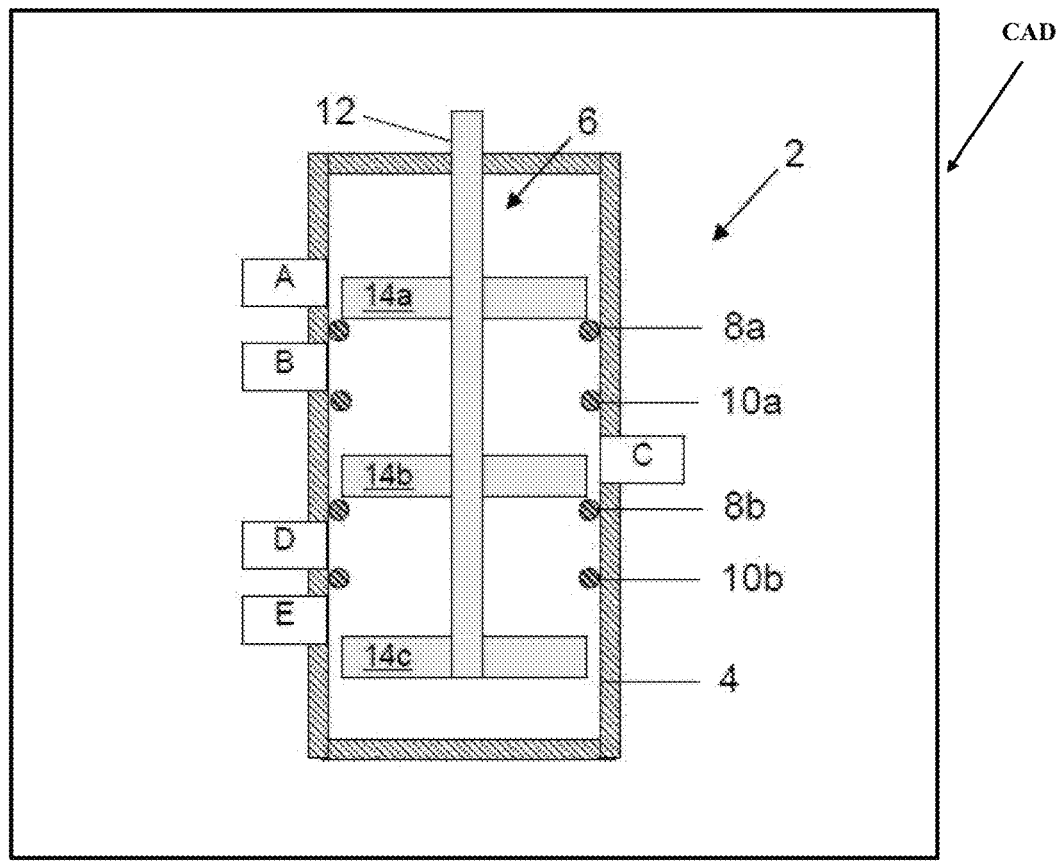
FIG. 19 is a cross-sectional view of a valve according to another embodiment of the invention.

The valve 2 is particularly suited to application in a cough assist device CAD (e.g., as shown in FIG. 19). In this application, the valve 2 is used to apply a positive pressure to a patient's lungs during an insufflation phase and to apply a negative pressure to the patient's lungs during an exsufflation phase. Between the exsufflation phase and the next insufflation phase, a short pause is provided in which no pressure is applied to the patient's lungs. The valve 2 is therefore configured to supply either a positive pressure, a negative pressure, or no pressure.

The valve 2 is arranged so that port C is connected to the lungs of the patient. This may be via a mouthpiece or mask which is worn by the patient, or via a connection to a tracheotomy tube.

Port B is connected to a source of positive air pressure, whereas port D is connected to a source of negative air pressure (although the reverse configuration may be used). Ports A and E vent to ambient pressure.

The first position of the valve element 6 shown in FIG. 3 corresponds to the insufflation phase. In this position, the positive pressure provided at port B is in fluid communication with port C and thus air enters the lungs of the patient during the insufflation phase. On the other hand, the negative pressure provided at port D is sealed from port C and the patient by the sealing of the central valve member 14b against the upper surface of the second upper seal portion 8b. The negative pressure provided at port D instead vents to atmospheric pressure via port E.

The second position of the valve element 6 shown in FIG. 4 corresponds to the exsufflation phase. In this position, the negative pressure provided at port D is in fluid communication with port C and thus extracts the air volume introduced during the insufflation phase from the lungs, and, along with it, any secretions. On the other hand, the positive pressure provided at port B is sealed from port C and the patient by the sealing of the central valve member 14b against the lower surface of the first lower seal portion 10a. The positive pressure provided at port B instead vents to atmospheric pressure via port A.

The third position of the valve element 6 shown in FIG. 5 corresponds to the pause phase. In this position, both the positive pressure provided at port B and the negative pressure provided at port D vent to atmospheric pressure via ports A and E respectively. Consequently, no pressure is applied to port C and the patient.

During the insufflation phase, the pressure at port C may gradually increase by moving the valve element 6 from the (zero pressure) third position shown in FIG. 5 to the (fully open) first position shown in FIG. 3.

Figure 6:
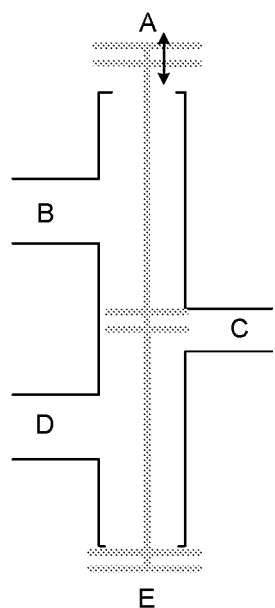
FIG. 6 is a schematic view of an oscillation of the valve.

An oscillation in pressure and flow may also be superimposed during the insufflation and/or exsufflation phases to loosen secretions in the patient's airways. FIG. 6 shows an oscillation of the valve element 6 during the exsufflation phase. As shown, the valve element 6 oscillates between the (fully open) second position shown in FIG. 4 and a position which is slightly toward the (zero pressure) third position shown in FIG. 5. This varies the pressure applied to port C. A corresponding oscillation may also be applied during the insufflation phase between the (fully open) first position shown in FIG. 3 and a position which is slightly toward the (zero pressure) third position shown in FIG. 5. The amplitude and frequency of the oscillation may be set to enhance the removal of secretions from the lungs, whilst minimizing discomfort for the patient.

As described previously, the seal portions 8, 10 are deformable under force applied by the respective valve member. The deformation of the seal portions 8, 10 is able to counteract deviations in the positions of the valve members 14a-14c and/or the seal portions 8, 10.

For example, the upper valve member 14a and the central valve member 14b may be affixed to the stem 12 such that they are spaced apart from one another by a distance which is different from that desired. Such deviations may result from manufacturing tolerances or thermal expansion or contraction of the components (particularly the stem 12), for example.

Where the spacing between the upper valve member 14a and the central valve member 14b is greater than desired, the central valve member 14b will contact the upper surface of the second upper seal portion 8b prior to the upper valve member 14a contacting the upper surface of the first upper seal portion 8a.

Ordinarily, in this situation, the upper valve member 14a would be spaced from the upper surface of the first upper seal portion 8a and thus would not be able to seal against the first upper seal portion 8a. Consequently, air from port B would leak past the upper valve member 14a to port A, thus reducing the air pressure delivered to port C. However, the second upper seal portion 8b is able to deform under a force applied by the central valve member 14b and thus can counteract the deviation in the distance between the upper valve member 14a and the central valve member 14b.

The deformation of the second upper seal portion 8b translates the upper surface of the second upper seal portion 8b in the direction of movement of the valve element 6. Consequently, the deformation of the second upper seal portion 8b effectively increases the distance between the upper surface of the first upper seal portion 8a and the upper surface of the second upper seal portion 8b. This allows the upper valve member 14a to be brought into contact with the upper surface of the first upper seal portion 8a, and thus provides an effective seal between the upper valve member 14a and the first upper seal portion 8a, and between the central valve member 14b and the second upper seal portion 8b.

On the other hand, where the spacing between the upper valve member 14a and the central valve member 14b is smaller than desired, the upper valve member 14a will contact the upper surface of the first upper seal portion 8a prior to the central valve member 14b contacting the upper surface of the second upper seal portion 8b.

The first upper seal portion 8a is able to deform under a force applied by the upper valve member 14a and thus can counteract the deviation in the distance between the upper valve member 14a and the central valve member 14b.

The deformation of the first upper seal portion 8a translates the upper surface of the first upper seal portion 8a in the direction of movement of the valve element 6. Consequently, the deformation of the first upper seal portion 8a effectively decreases the distance between the upper surface of the first upper seal portion 8a and the upper surface of the second upper seal portion 8b. This allows the central valve member 14b to be brought into contact with the upper surface of the second upper seal portion 8b, and thus provides an effective seal between the upper valve member 14a and the first upper seal portion 8a, and between the central valve member 14b and the second upper seal portion 8b.

Similarly, the first and second lower seal portions 10a, 10b are deformable to counteract deviations in the distance between the central valve member 14b and the lower valve member 14c.

There may also be deviations in the positions (or sizes) of the seal portions 8, 10 themselves. The deformation of the seal portions 8, 10 is again able to counteract these deviations so as to ensure that an effective seal is provided between the valve members 14a-14c and the seal portions 8, 10.

The valve element 6 is translated relative to the housing 4 using a linear actuator, such as a voice coil linear motor. This provides extremely quick and accurate translation of the valve element 6 between the operating positions. As described previously, the valve members 14a-14c are sized such that they do not contact the inner surface of the housing 4. Consequently, very little resistance is provided against the movement of the valve element 6 until the valve members 14a-14c contact the seal portions 8, 10. When operating in the first or second position, the actuator may translate the valve element 6 until a predetermined resistive force is offered by the seal portions 8, 10. The predetermined resistive force may be set so as to ensure that, in the first position, the upper and central valve members 14a, 14b are both sealed against the first and second upper seal portions 8a, 8b and that, in the second position, the central and lower valve members 14b, 14c are both sealed against the first and second lower seal portions 10a, 10b.

A valve 102 according to a second embodiment of the invention will now be described with reference to FIG. 7.

The valve 102 has a similar construction to the valve 2. Consequently, the following description of the valve 102 will focus primarily on the differences between the first and second embodiments.

As per the valve 2 of the first embodiment, the valve 102 comprises a housing 104 in which a movable valve element 106 is disposed.

The housing 104 is identical to the housing 4 of the first embodiment and comprises ports A-E provided in the wall of the housing 104 and a plurality of seal portions affixed to the housing 104. As per the first embodiment, the seal portions comprise an upper pair formed by a first upper seal portion 108a and a second upper seal portion 108b, and a lower pair formed by a first lower seal portion 110a and a second lower seal portion 110b.

Like the valve element 6, the valve element 106 comprises a central stem 112 and a plurality of valve members 114a-114c, which are provided on the stem 12. However, in the movable valve element 106, the upper and lower valve members 114a, 114c are much thinner than the central valve member 114b. Consequently, the upper and lower valve members 114a and 114c are flexible and are able to deform under force.

The valve members 114a-114c are sized so that they may not pass through the seal portions. The seal portions therefore act as stops which limit the movement of the valve element 106.

The deformation of the upper and lower valve members 114a, 114c is able to counteract deviations in the positions of the valve members 114a-114c and/or the seal portions 108, 110.

Where the spacing between the upper valve member 114a and the central valve member 114b is smaller than desired, the upper valve member 114a will contact the upper surface of the first upper seal portion 8a prior to the central valve member 114b contacting the upper surface of the second upper seal portion 108b.

Ordinarily, in this situation, the central valve member 114b would be spaced from the upper surface of the second upper seal portion 108b and thus would not be able to seal against the second upper seal portion 108b. Consequently, ports B and C would be exposed to the negative pressure of port D. However, the upper valve member 114a is able to deform under a force applied by the movement of the upper valve member 114a relative to the first upper seal portion 108a, and thus can counteract the deviation in the distance between the upper valve member 114a and the central valve member 114b.

At rest, the upper valve member 114a assumes a substantially planar profile in which a radially inner portion adjacent the stem 112 is aligned with a radially outer periphery of the upper valve member 114a.

Figure 7:
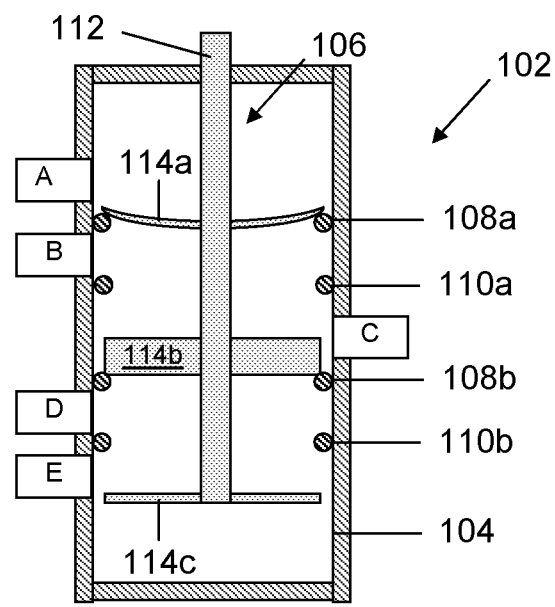
FIG. 7 is a cross-sectional view of a valve according to a second embodiment of the invention.

As shown in FIG. 7, the movement of the upper valve member 114a relative to the first upper seal portion 108a causes the upper valve member 114a to be deformed such that the outer periphery of the upper valve member 114a is no longer aligned with the radially inner portion. The outer periphery of the upper valve member 114a is deflected away from the central valve member 114b.

This effectively increases the distance between the lower surfaces of the upper valve member 114a and the central valve member 114b at the point where they contact the first and second upper seal portions 108a, 108b. This allows the central valve member 114b to be brought into contact with the upper surface of the second upper seal portion 108b, and thus provides an effective seal between the upper valve member 114a and the first upper seal portion 108a, and between the central valve member 114b and the second upper seal portion 108b.

Similarly, the lower valve member 114c is deformable to counteract deviations in the distance between the central valve member 114b and the lower valve member 114c.

Although only the upper and lower valve members 114a, 114c have been described as being deformable, the central valve member 114b may alternatively or additionally be deformable.

The central valve member 114b may be deformed either toward the upper valve member 114a (in the first position) or toward the lower valve member 114c (in the second position). Accordingly, the deformation of the central valve member 114b is able to counteract deviations which result in the distance between the central valve member 114b and the upper or lower valve member 114a, 114c being greater than desired. This would otherwise cause the upper or lower valve member 114a, 114c to be spaced from the upper surface of the first upper seal portion 108a or the lower surface of the second lower seal portion 110b, respectively.

Where only the central valve member 114b or the upper and lower valve members 114a, 114c is/are deformable, the spacing between the central valve member 114b and the upper valve member 114a, and between the central valve member 114b and the lower valve member 114c may be configured such that an effective seal is formed between the upper valve member 114a and the first upper seal portion 108a, and between the central valve member 114b and the second upper seal portion 108b over the range of anticipated deviations.

Specifically, where only the central valve member 114b is deformable, the deformation is able to counteract deviations which result in the distance between the central valve member 114b and the upper or lower valve member 114a, 114c being greater than desired. Therefore, the spacing between the central valve member 114b and the upper valve member 114a, and between the central valve member 114b and the lower valve member 114c is set such that under the maximum anticipated deviation (i.e. based on manufacturing tolerances, thermal expansion or contraction, etc.) which results in the spacing being smaller than desired, an effective seal is still formed between the upper valve member 114a and the first upper seal portion 108a, and between the central valve member 114b and the second upper seal portion 108b. Under the maximum anticipated deviation, the central valve member 114b may be subject to only minimal resistive force by the second upper seal portion 108b (in the first position) or the first lower seal portion 110a (in the second position) such that the central valve member 114b is substantially underformed or only slightly deformed. Consequently, all other deviations from the desired spacing result in the central valve member 114b being deformed to a greater extent.

On the other hand, where only the upper and lower valve members 114a, 114c are deformable, the deformation is able to counteract deviations which result in the distance between the central valve member 114b and the upper or lower valve member 114a, 114c being smaller than desired. Therefore, the spacing between the central valve member 114b and the upper valve member 114a, and between the central valve member 114b and the lower valve member 114c is set such that under the maximum anticipated deviation (i.e. based on manufacturing tolerances, thermal expansion or contraction, etc.) which results in the spacing being greater than desired, an effective seal is still formed between the upper valve member 114a and the first upper seal portion 108a, and between the central valve member 114b and the second upper seal portion 108b. Under the maximum anticipated deviation, the upper valve member 114a (in the first position) or the lower valve member 114c (in the second position) may be subject to only minimal resistive force by the first upper seal portion 108a or the second lower seal portion 110b respectively such that the upper or lower valve member 114a, 114c is substantially undeformed or only slightly deformed. Consequently, all other deviations from the desired spacing result in the upper or lower valve member 114a, 114c being deformed to a greater extent.

There may also be deviations in the positions (or sizes) of the seal portions 108, 110. The deformation of the valve members 114a-114c is again able to counteract these deviations so as to ensure that an effective seal is provided between the valve members 114a-114c and the seal portions 108, 110. The deformation of the central valve member 114b is able to counteract deviations which result in the upper surfaces of the first and second upper seal portions 108a, 108b and the lower surfaces of the first and second lower seal portions 110a, 110b being respectively spaced closer to one another than desired. Conversely, the deformation of the upper and lower valve members 114a, 114c is able to counteract deviations which result in the upper surfaces of the first and second upper seal portions 108a, 108b and the lower surfaces of the first and second lower seal portions 110a, 110b being respectively spaced further from one another than desired.

As per the valve 2 of the first embodiment, the seal portions 108, 110 may also be deformable under force applied by the respective valve member. The combined deformation of the seal portions 108, 110 and the valve members 114a-114c can counteract larger deviations in the positions of the seal portions 108, 110 and the valve members 114a-114c.

The deformable valve members may be pre-curved such that they are deformed towards a planar configuration. This may increase the resistance of the valve members to deformation and thus provide a bias force which acts to return the valve element 106 to the third position from the first and/or second positions.

Figure 8:
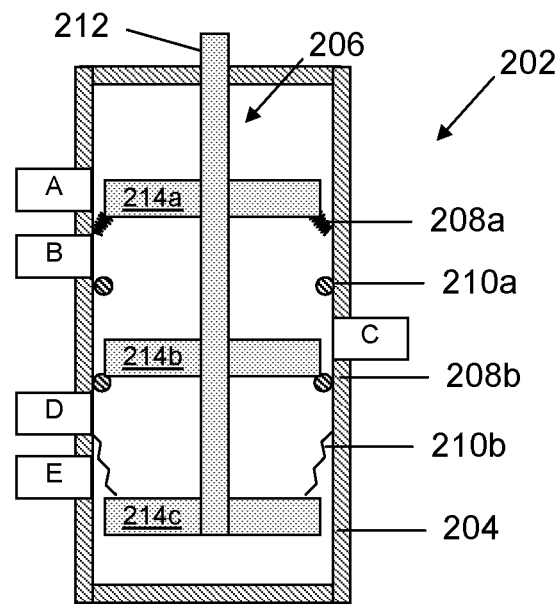
FIG. 8 is a cross-sectional view of a valve according to a third embodiment of the invention.

A valve 202 according to a third embodiment of the invention will now be described with reference to FIG. 8.

The valve 202 has a similar construction to the valve 2. Consequently, the following description of the valve 202 will focus primarily on the differences between the first and second embodiments.

As per the valve 2 of the first embodiment, the valve 202 comprises a housing 204 in which a movable valve element 206 is disposed.

The housing 204 is similar to the housing 4 of the first embodiment and comprises ports A-E provided in the wall of the housing 204 and a plurality of seal portions affixed to the housing 204. As per the first embodiment, the seal portions comprise an upper pair formed by a first upper seal portion 208a and a second upper seal portion 208b, and a lower pair formed by a first lower seal portion 210a and a second lower seal portion 210b. However, whilst the second upper seal portion 208b and the first lower seal portion 210a are each formed by an O-ring (or another similar type of seal), the first upper seal portion 208a and the second lower seal portion 208b are each formed by a bellows member.

The bellows member of the first upper seal portion 208a is connected at one end to the upper valve member 214a and at the other end to the inner surface of the housing 204 at a position which is between ports A and B. Similarly, the bellows member of the second lower seal portion 210b is connected at one end to the lower valve member 214c and at the other end to the inner surface of the housing 204 at a position which is between ports D and E.

Each of the bellows members is constructed from a tubular length of flexible material, such as rubber, which is formed into a series of convolutions. The convolutions allow the length of the bellows member to increase or decrease. The bellows member may taper slightly such that the end of the bellows member which is connected to the housing 204 has a greater diameter than the end which is connected to the upper or lower valve member 214a, 214c.

Figure 9:
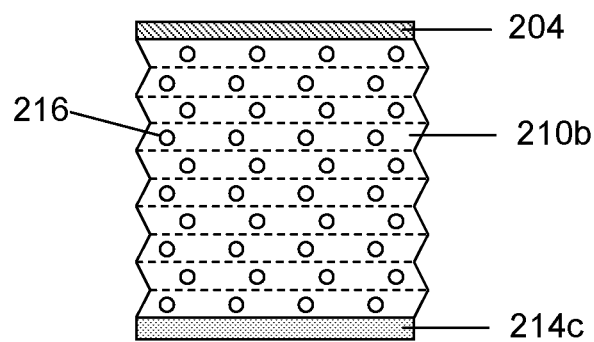
FIG. 9 is an enlarged view of the valve shown in FIG. 8, showing a bellows member in an expanded state.

FIG. 9 shows the bellows member of the second lower seal portion 210b when the valve element 206 is in the first position. In this position, the lower valve member 214c is spaced away from port D and the position at which the bellows member connects to the housing 204. Accordingly, the bellows member is in an expanded state.

As shown in FIG. 9, a plurality of holes 216 are formed in each of the convolutions of the bellows member. The holes 216 pass entirely through the thickness of the material of the bellows member and thus, in the expanded state, enable fluid communication across the bellows member (i.e. from the inside of the bellows member to the outside of the bellows member, and vice versa).

Figure 10:
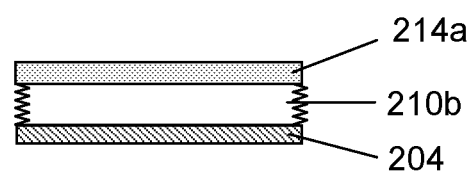
FIG. 10 is an enlarged view of the valve shown in FIG. 8, showing a bellows member in a compressed state.

FIG. 10 shows the bellows member of the first upper seal portion 208a when the valve element 206 is in the first position. In this position, the upper valve member 214a is adjacent port B and the position at which the bellows member connects to the housing 204. Accordingly, the bellows member is in a contracted state.

In the contracted state, the convolutions of the bellows member are forced together such that the respective inner and outer surfaces of adjacent convolutions contact one another.

As shown in FIG. 9, the holes 216 of adjacent convolutions are offset from one another. Consequently, in the contracted state, the holes 216 of each convolution are covered by the surface of an adjacent convolution. Accordingly, in the contracted state, fluid communication is not permitted across the bellows member.

For clarity, the arrangement of valve element 206 and the permitted flow passages will now be described for the first, second and third positions of the valve element 206.

In the first position of the valve element 206, the upper valve member 214a is sealed against the housing 204 since the bellows member of the first upper seal portion 208a is in the contracted state, the central valve member 214b is sealed against the upper surface of the second upper seal portion 208b, and the lower valve member 214c is not sealed against the housing 204 since the bellows member of the second lower seal portion 210b is in the expanded state.

In the first position, ports B and C are in fluid communication with one another, and ports D and E are in fluid communication with one another via the holes 216 in the bellows member of the second lower seal portion 210b. In contrast, ports A and B are not in fluid communication with one another since they are sealed from one another by the bellows member of the first upper seal portion 208a.

In the second position of the valve element 206, the upper valve member 214a is not sealed against the housing 204 since the bellows member of the first upper seal portion 208a is in the expanded state, the central valve member 214b is sealed against the lower surface of the first lower seal portion 210a, and the lower valve member 214c is sealed against the housing 204 since the bellows member of the second lower seal portion 210b is in the contracted state.

In the second position, ports A and B are in fluid communication with one another via the holes 216 in the bellows member of the first upper seal portion 208a, and ports C and D are in fluid communication with one another. In contrast, ports D and E are not in fluid communication with one another since they are sealed from one another by the bellows member of the second lower seal portion 210b.

In the third position of the valve element 206, the upper valve member 214a and the lower valve member 214c are not sealed against the housing 204 since the bellows members of the first upper seal portion 208a and the second lower seal portion 210b are in a partially expanded state. In the partially expanded state, the holes 216 are sufficiently unobstructed so as to allow fluid communication across the bellows members. The central valve member 214b is spaced from both the lower surface of the first lower seal portion 210a and the upper surface of second upper seal portion 208b.

In the third position, none of the valve members 214a-214c are sealed against the housing by the seal portions 208, 210. Consequently, ports A-E are all in fluid communication with one another.

As described above, in the contracted state, the holes 216 of the bellows member are obstructed and thus the bellows member forms a seal. An adequate seal is provided over a range of contracted states (referred to as the sealed range of the bellows member). In other words, the effective length of the bellows member may vary whilst maintaining an adequate seal.

The bellows members of the first upper seal portion 208a and the second lower seal portion 210b are thus able to deform over the sealed range so as to counteract deviations in the positions of the valve members 214a-214c and/or the seal portions 208, 210.

Although only the first upper seal portion 208a and the second lower seal portion 210b have been described as being formed by bellows members, the second upper seal portion 208b and the first lower seal portion 210a may alternatively or additionally be formed by bellows.

In an alternative arrangement (not illustrated), the bellows members may be replaced by a tubular seal formed of a stretchable material having a plurality of holes formed therethrough. In the contracted state the holes are closed and in the expanded state the holes are open.

The size of the holes in the stretchable material may vary proportionally with the position of the valve element 206. Therefore, the resistance of the stretchable material to fluid flow can be configured to vary with the position of the valve element 206. For example, the stretchable material may be configured so that the resistance to fluid flow varies linearly with the position of the valve element 206.

Figure 11:
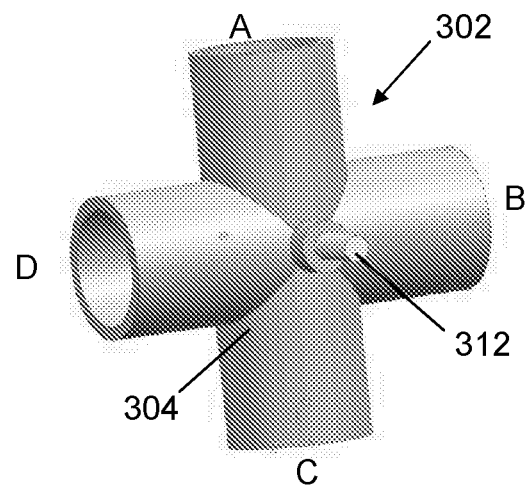
FIG. 11 is a perspective view of second type of valve in which the invention may be applied.
Figure 12:
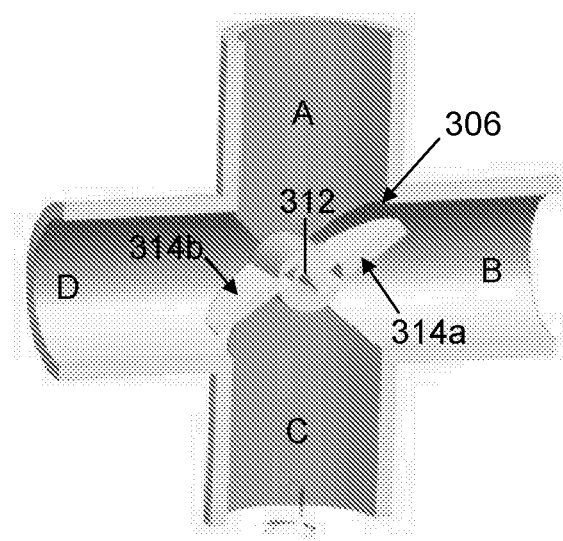
FIG. 12 is a cross-sectional view of the valve shown in FIG. 11.

FIGS. 11 and 12 show a valve 302 according to a fourth embodiment of the invention. The valve 302 of the fourth embodiment differs from the previous embodiments in that the inventive concept is applied in a rotational valve, such as a butterfly valve.

The valve 302 comprises a housing 304 in which a movable valve element 306 is disposed. The housing 304 is formed by four tubular conduits which all lie in the same plane and which are joined at the centre of the housing 304. The end of each of the conduits is mitred at 90° (referred to herein as an end quadrant) so that the conduits can be arranged in a cruciform and adjoin one another to form a fluid-tight housing. The four tubular conduits define ports A-D. Ports A and C are positioned opposite one another and ports B and D are positioned opposite one another.

The end quadrants of the four conduits define a generally spherical chamber which will be described further below.

Figure 13:
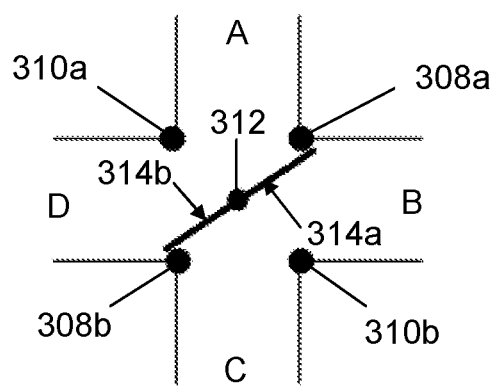
FIG. 13 is a schematic view of a valve according to a fourth embodiment of the invention in a first position.
Figure 14:
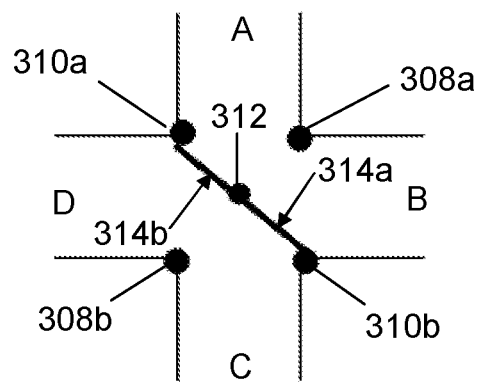
FIG. 14 is a schematic view of the valve shown in FIG. 13 in a second position.

A plurality of seal portions are affixed to the housing 304 within the chamber (see FIGS. 13 and 14). The seal portions comprise a right-diagonal pair formed by a first right-diagonal seal portion 308a and a second right-diagonal seal portion 308b, and a left-diagonal pair formed by a first left-diagonal seal portion 310a and a second left-diagonal seal portion 310b.

The first right-diagonal seal portion 308a is substantially semi-circular and is connected to the housing 304 along the intersection between the end quadrants of ports A and B. The first right-diagonal seal portion 308a therefore seals port A from port B. Similarly, the second right-diagonal seal portion 308b is substantially semi-circular and is connected to the housing 304 along the intersection between the end quadrants of ports C and D. The second right-diagonal seal portion 308b therefore seals port C from port D. The right-diagonal pair of seal portions 308 thus separates ports B and C from ports A and D.

The first left-diagonal seal portion 310a is substantially semi-circular and is connected to the housing 304 along the intersection between the end quadrants of ports A and D. The first left-diagonal seal portion 310a therefore seals port A from port D. Similarly, the second left-diagonal seal portion 310b is substantially semi-circular and is connected to the housing 304 along the intersection between the end quadrants of ports B and C. The second left-diagonal seal portion 310b therefore seals port B from port C. The left-diagonal pair of seal portions 310 thus separates ports A and B from ports C and D.

The right-diagonal pair of seal portions 308 and the left-diagonal pair of seal portions 310 are offset from one another by an angular distance of approximately 90° and intersect one another at the centre of the chamber.

The movable valve element 306 comprises a central stem 312 to which a first valve member 314a and a second valve member 314b are coupled. Each of the first and second valve members 314a, 314b is a substantially semi-circular disc. The first and second valve members 314a, 314b thus have a complementary shape to the cross-section of the chamber defined by the end quadrants of the conduits. The first valve member 314a and the second valve member 314b are coupled to the stem 312 at diametrically opposed positions. The first and second valve members 314a, 314b are arranged so as to extend from the stem 312 in directions which are parallel but offset from one another, as shown in FIG. 12.

The first and second valve members 314a, 314b are sized so that they may not pass through the seal portions 308, 310. The seal portions 308, 310 therefore act as stops which limit the movement of the valve element 306. Further, whilst the first and second valve members 314a, 314b have a complementary shape to the chamber, they are sized slightly smaller such that they do not ordinarily contact the inner surface of the wall of the housing 314.

The positions of the first and second valve members 314a, 314b will now be described with reference to the seal portions 308, 310. The first valve member 314a is provided between the first right-diagonal seal portion 308a and the second left-diagonal seal portion 310b and is configured to seal against either the first right-diagonal seal portion 308a or the second left-diagonal seal portion 310b. The first valve member 314a is therefore permitted to move within the end quadrant of port B. The second valve member 314b is provided between the second right-diagonal seal portion 308b and the first left-diagonal seal portion 310a and is configured to seal against either the second right-diagonal seal portion 308b or the first left-diagonal seal portion 310a. The second valve member 314b is therefore permitted to move within the end quadrant of port D.

The valve element 306 is rotatable relative to the housing 304 so as to adjust the positions of the first and second valve members 314a, 314b. As described previously, the valve members 314a, 314b are sized so that they may not pass through the seal portions 308, 310. Accordingly, the seal portions 308, 310 limit the movement of the valve element 306.

The positions of the valve element 306 will now be described with reference to the schematic illustrations provided in FIGS. 13 to 16.

FIG. 13 shows a first position of the valve element 306 in which the first valve member 314a is sealed against the first right-diagonal seal portion 308a, and the second valve member 314b is sealed against the second right-diagonal seal portion 308b. As shown in FIG. 13, the first and second valve members 314a, 314b seal against opposing sides of the first and second right-diagonal seal portions 308a, 308b.

In the first position, ports A and D are in fluid communication with one another, and ports B and C are in fluid communication with one another. The first and second valve members 314a, 314b thus separate ports A and D from ports B and C.

FIG. 14 shows a second position of the valve element 306 in which the first valve member 314a is sealed against the second left-diagonal seal portion 310b, and the second valve member 314b is sealed against the first left-diagonal seal portion 310a. As shown in FIG. 14, the first and second valve members 314a, 314b seal against opposing sides of the first and second left-diagonal seal portions 310a, 310b.

In the second position, ports A and B are in fluid communication with one another, and ports C and D are in fluid communication with one another. The first and second valve members 314a, 314b thus separate ports A and B from ports C and D.

Figure 15:
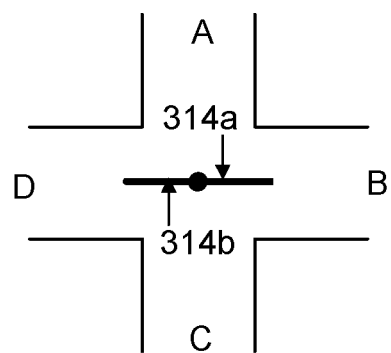
FIG. 15 is a schematic view of the valve of FIG. 13 in a third position.

FIG. 15 shows a third position of the valve element 306 which is midway between the first and second positions described previously. In the third position, the first valve member 314a is spaced from both the first right-diagonal seal portion 308a and the second left-diagonal seal portion 310b, and the second valve member 314b is spaced from both the second right-diagonal seal portion 308b and the first left-diagonal seal portion 310a.

In the third position, neither of the first and second valve members 314a, 314b are sealed against the seal portions 308, 310. Consequently, ports A-D are all in fluid communication with one another.

Figure 20:
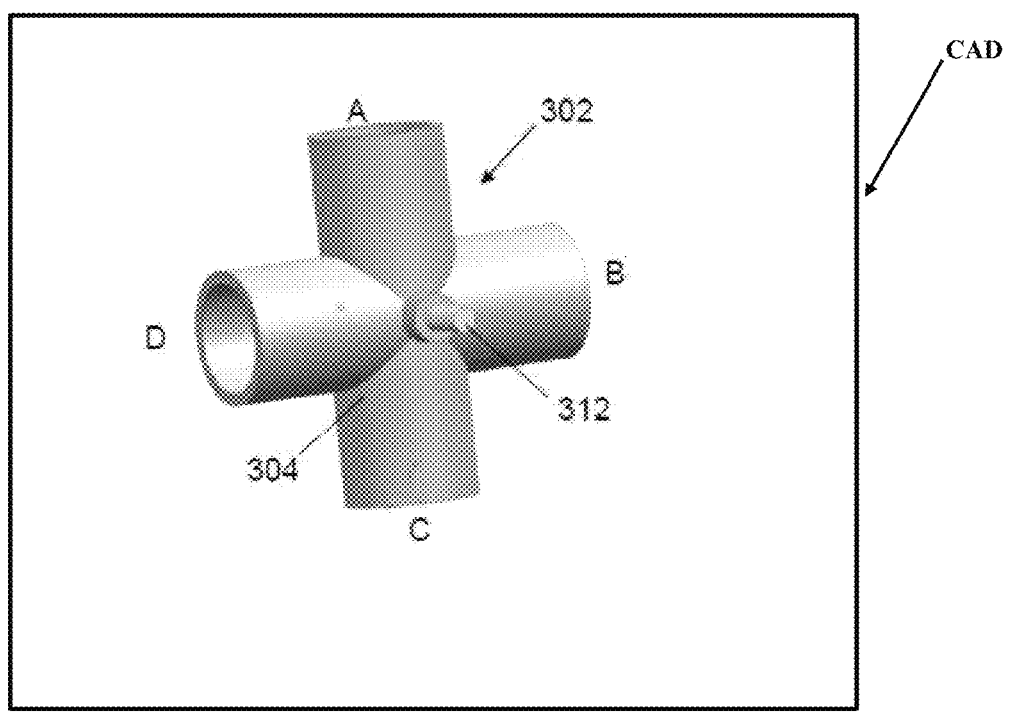
FIG. 20 is a perspective view of a valve according to yet another embodiment of the invention.

The valve 302 is particularly suited to application in a cough assist device. CAD (e.g., as shown in FIG.20) In this application, the valve 302 is used to apply a positive pressure to a patient's lungs during an insufflation phase and to apply a negative pressure to the patient's lungs during an exsufflation phase. Between the exsufflation phase and the next insufflation phase, a short pause is provided in which no pressure is applied to the patient's lungs. The valve 302 is therefore configured to supply either a positive pressure, a negative pressure, or no pressure.

The valve 302 is arranged so that port C is connected to the lungs of the patient. This may be via a mouthpiece or mask which is worn by the patient, or via a connection to a tracheotomy tube.

Port B is connected to a source of positive air pressure, whereas port D is connected to a source of negative air pressure (although the reverse configuration may be used). Port A vents to ambient pressure.

The first position of the valve element 306 shown in FIG. 13 corresponds to the insufflation phase. In this position, the positive pressure provided at port B is in fluid communication with port C and thus air enters the lungs of the patient during the insufflation phase. On the other hand, the negative pressure provided at port D is sealed from port C and the patient by the sealing of the second valve member 314b against the second right-diagonal seal portion 308b and the sealing of the first valve member 314a against the first right-diagonal seal portion 308a. The negative pressure provided at port D instead vents to atmospheric pressure via port A.

The second position of the valve element 306 shown in FIG. 14 corresponds to the exsufflation phase. In this position, the negative pressure provided at port D is in fluid communication with port C and thus extracts the air volume introduced during the insufflation phase from the lungs, and, along with it, any secretions. On the other hand, the positive pressure provided at port B is sealed from port C and the patient by the sealing of the first valve member 314a against the second left-diagonal seal portion 310b and the sealing of the second valve member 314b against the first left-diagonal seal portion 310a. The positive pressure provided at port B instead vents to atmospheric pressure via port A.

The third position of the valve element 306 shown in FIG. 15 corresponds to the pause phase. In this position, both the positive pressure provided at port B and the negative pressure provided at port D vent to atmospheric pressure via port A. Consequently, no pressure is applied to port C and the patient.

During the insufflation phase, the pressure at port C may gradually increase by moving the valve element 306 from the (zero pressure) third position shown in FIG. 15 to the (fully open) first position shown in FIG. 13.

Figure 16:
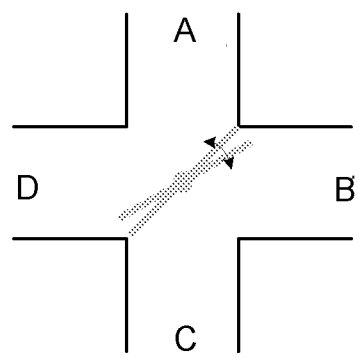
FIG. 16 is a schematic view of the valve of FIG. 13 in an oscillation phase.

An oscillation in pressure and flow may also be superimposed during the insufflation and/or exsufflation phases to loosen secretions in the patient's airways. FIG. 16 shows an oscillation of the valve element 306 during the insufflation phase. As shown, the valve element 306 oscillates between the (fully open) first position shown in FIG. 13 and a position which is slightly toward the (zero pressure) third position shown in FIG. 15. This varies the pressure applied to port C. A corresponding oscillation may also be applied during the exsufflation phase between the (fully open) second position shown in FIG. 14 and a position which is slightly toward the (zero pressure) third position shown in FIG. 15. The amplitude and frequency of the oscillation may be set to enhance the removal of secretions from the lungs, whilst minimizing discomfort for the patient.

In a similar manner to the seal portions 8, 10 of the first embodiment, the seal portions 308, 310 are deformable under force applied by the first and second valve members 314a, 314b. The deformation of the seal portions 308, 310 is able to counteract deviations in the positions of the valve members 314a, 314b and/or the seal portions 308, 310.

For example, the first and second valve members 314a, 314b may be affixed to the stem 312 such that they are spaced apart from one another by an angular distance which is different from that desired (i.e. where the first and second valve members 314a, 314b are not parallel with one another). Such deviations may result from manufacturing tolerances or distortion of the valve members, for example.

In the first position, where the angular distance in the direction of movement (from the second position to the first position) between the first valve member 314a and the second valve member 314b is greater than desired (i.e. in an anticlockwise direction from the first valve member 314a to the second valve member 314b), the second valve member 314b will contact the second right-diagonal seal portion 308b prior to the first valve member 314a contacting the first right-diagonal seal portion 308a.

Ordinarily, in this situation, the first valve member 314a would be spaced from the first right-diagonal seal portion 308a and thus would not be able to seal against the first right-diagonal seal portion 308a. Consequently, air from port B would leak past the first valve member 314a to port A, thus reducing the air pressure delivered to port C. However, the second right-diagonal seal portion 308b is able to deform under a force applied by the second valve member 314b and thus can counteract the deviation in the distance between the first and second valve members 314a, 314b.

The deformation of the second right-diagonal seal portion 308b translates the opposing surface of the second right-diagonal seal portion 308b in the direction of rotation of the valve element 306. Consequently, the deformation of the second right-diagonal seal portion 308b effectively increases the angular distance (measured in the same manner as for the first and second valve members 314a, 314b) between the opposing surface of the first right-diagonal seal portion 308a and the opposing surface of second right-diagonal seal portion 308b. This allows the first valve member 314a to be brought into contact with the surface of the first right-diagonal seal portion 308a, and thus provides an effective seal between the first valve member 314a and the first right-diagonal seal portion 308a, and between the second valve member 314b and the second right-diagonal seal portion 308b.

On the other hand, where the angular distance between the first valve member 314a and the second valve member 314b is smaller than desired, the first valve member 314a will contact the first right-diagonal seal portion 308a prior to the second valve member 314b contacting the second right-diagonal seal portion 308b.

The first right-diagonal seal portion 308a is able to deform under a force applied by the first valve member 314a and thus can counteract the deviation in the distance between the first valve member 314a and the second valve member 314b.

The deformation of the first right-diagonal seal portion 308a translates the opposing surface of the first right-diagonal seal portion 308a in the direction of rotation of the valve element 306. Consequently, the deformation of the first right-diagonal seal portion 08a effectively decreases the distance between the opposing surface of the first right-diagonal seal portion 308a and the opposing surface of the second right-diagonal seal portion 308b. This allows the second valve member 314b to be brought into contact with the surface of the second right-diagonal seal portion 308b, and thus provides an effective seal between the first valve member 314a and the first right-diagonal seal portion 308a, and between the second valve member 314b and the second right-diagonal seal portion 308b.

Similarly, the first and second left-diagonal seal portions 310a, 310b are deformable to counteract deviations in the angular distance in the direction of movement (from the first position to the second position) between the first valve member 314a and the second valve member 314b (i.e. in an clockwise direction from the first valve member 314a to the second valve member 314b) when the valve element 306 is in the second position.

There may also be deviations in the positions (or sizes) of the seal portions 308, 310 themselves. The deformation of the seal portions 308, 310 is again able to counteract these deviations so as to ensure that an effective seal is provided between the valve members 314a, 314b and the seal portions 308, 310.

The valve element 306 is rotated relative to the housing 304 using a rotary actuator, such as a voice coil rotary motor. This provides extremely quick and accurate rotation of the valve element 306 between the operating positions. As described previously, the valve members 314a, 314b are sized such that they do not contact the inner surface of the housing 304. Consequently, very little resistance is provided against the movement of the valve element 306 until the valve members 314a, 314b contact the seal portions 308, 310. When operating in the first or second position, the actuator may rotate the valve element 306 until a predetermined resistive force is offered by the right-diagonal or left-diagonal seal portions 308, 310. The predetermined resistive force may be set so as to ensure that, in the first position, the first and second valve members 314a, 314b are both sealed against the first and second right-diagonal seal portions 308a, 308b and that, in the second position, the first and second valve members 314a, 314b are both sealed against the first and second left-diagonal seal portions 310a, 310b.

Although the first and second valve members 314a, 314b have been described as being offset from one another, they may alternatively be aligned with one another and the seal portions may instead be offset from one another.

Further, although the seal portions 308, 310 have been described as being located at the intersection of the adjacent ports, they may be located on either side of the intersection.

Figure 17:
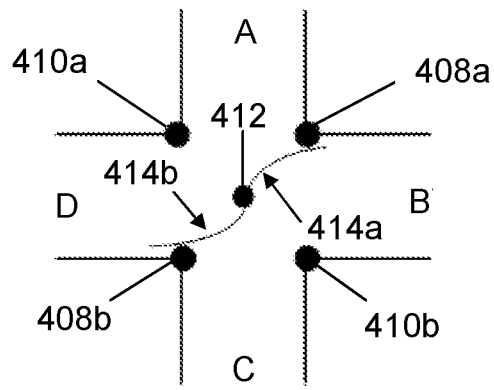
FIG. 17 is a schematic view of a valve according to a fifth embodiment of the invention in a first position.
Figure 18:
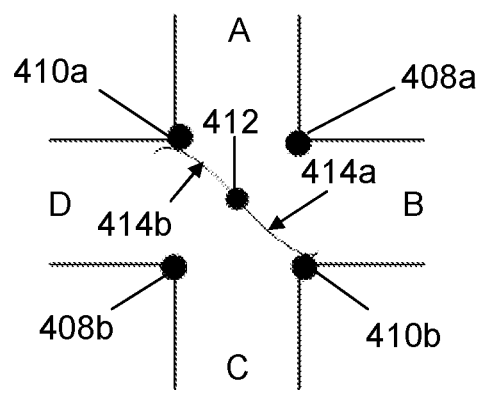
FIG. 18 is a schematic view of the valve shown in FIG. 17 in a second position.

FIGS. 17 and 18 show a valve 402 according to a fifth embodiment of the invention. As per the valve 302 of the previous embodiment, the valve 402 is a rotational valve, such as a butterfly valve. The valve 402 corresponds to a rotational implementation of the second embodiment described previously.

The valve 402 has a similar construction to the valve 302. Consequently, the following description of the valve 402 will focus primarily on the differences between the fourth and fifth embodiments.

As per the valve 302 of the fourth embodiment, the valve 302 comprises a housing 404 in which a movable valve element 406 is disposed.

FIG. 17 shows the valve element 406 in the first position (corresponding to the insufflation phase), whereas FIG. 18 shows the valve element 406 in the second position (corresponding to the exsufflation phase). The valve element 406 can also assume the third position shown in FIG. 15 for the valve 302 (corresponding to the pause phase) and may oscillate as shown in FIG. 16 for the valve 302.

The housing 404 is identical to the housing 304 of the fourth embodiment and comprises ports A-D defined by four tubular conduits and a plurality of seal portions affixed to the housing 404 within the chamber. As per the fourth embodiment, the seal portions comprise a right-diagonal pair formed by a first right-diagonal seal portion 408a and a second right-diagonal seal portion 408b, and a left-diagonal pair formed by a first left-diagonal seal portion 410a and a second left-diagonal seal portion 410b.

Like the valve element 306, the valve element 406 comprises a central stem 412 to which a first valve member 414a and a second valve member 414b are coupled. However, in the movable valve element 406, the first and second valve members 414a, 414b are thinner and thus are able to flex and deform under force.

The first and second valve members 414a, 414b are sized so that they may not pass through the seal portions 408, 410. The seal portions 408, 410 therefore act as stops which limit the movement of the valve element 406.

The deformation of the first and second valve members 414a, 414b is able to counteract deviations in the positions of the valve members 414a, 414c and/or the seal portions 408, 410.

In the first position, where the angular distance in the direction of movement (from the second position to the first position) between the first valve member 414a and the second valve member 414b is greater than desired (i.e. in an anticlockwise direction from the first valve member 414a to the second valve member 414b), the second valve member 414b will contact the second right-diagonal seal portion 408b prior to the first valve member 414a contacting the first right-diagonal seal portion 408a.

Ordinarily, in this situation, the first valve member 414a would be spaced from the first right-diagonal seal portion 408a and thus would not be able to seal against the first right-diagonal seal portion 408a. Consequently, air from port B would leak past the first valve member 414a to port A, thus reducing the air pressure delivered to port C. However, the second valve member 414b is able to deform under a force applied by the rotation of the valve element 406 and thus can counteract the deviation in the distance between the first and second valve members 414a, 414b.

At rest, the second valve member 414b assumes a substantially planar profile in which a radially inner portion adjacent the stem 412 is aligned with a radially outer periphery of the second valve member 414b.

As shown in FIG. 17, the movement of the second valve member 414b relative to the second right-diagonal seal portion 408b causes the second valve member 414b to be deformed such that the outer periphery of the second valve member 414b is no longer aligned with the radially inner portion. The outer periphery of the second valve member 414b is deflected away from the second right-diagonal seal portion 408b toward the first left-diagonal seal portion 410a.

This effectively increases the angular distance between the first valve member 414a and the second valve member 414b at the point where they contact the first and second right-diagonal seal portions 408a, 408b. This allows the first valve member 414a to be brought into contact with the surface of the first right-diagonal seal portion 408a, and thus provides an effective seal between the first valve member 414a and the first right-diagonal seal portion 408a, and between the second valve member 414b and the second right-diagonal seal portion 408b.

On the other hand, where the angular distance between the first valve member 414a and the second valve member 414b is smaller than desired, the first valve member 414a will contact the first right-diagonal seal portion 408a prior to the second valve member 414b contacting the second right-diagonal seal portion 408b.

At rest, the first valve member 414a assumes a substantially planar profile in which a radially inner portion adjacent the stem 412 is aligned with a radially outer periphery of the first valve member 414a.

The first valve member 414a is able to deform under a force applied by the rotation of the valve element 406 and thus can counteract the deviation in the distance between the first and second valve members 414a, 414b.

Specifically, the movement of the first valve member 414a relative to the first right-diagonal seal portion 408a causes the first valve member 414a to be deformed such that the outer periphery of the first valve member 414a is no longer aligned with the radially inner portion. The outer periphery of the first valve member 414a is deflected away from the first right-diagonal seal portion 408a toward the second left-diagonal seal portion 410b.

This effectively decreases the angular distance between the first valve member 414a and the second valve member 414b at the point where they contact the first and second right-diagonal seal portions 408a, 408b. This allows the second valve member 414b to be brought into contact with the surface of the second right-diagonal seal portion 408a, and thus provides an effective seal between the first valve member 414a and the first right-diagonal seal portion 408a, and between the second valve member 414b and the second right-diagonal seal portion 408b.

Similarly, the first and second valve members 414a, 414b are deformable to counteract deviations in the distance between the first valve member 414a and the second valve member 414b when the valve element 406 is in the second position.

Although both of the first and second valve members 414a, 414b have been described as being flexible, only one of the first and second valve members 414a, 414b need be so. As described above, the deformation of the first valve member 414a is able to counteract deviations which result in the angular distance in the direction of movement between the first valve member 414a and the second valve member 414b being smaller than desired. Conversely, the deformation of the second valve member 414b is able to counteract deviations which result in the angular distance in the direction of movement between the first valve member 414a and the second valve member 414b being greater than desired.

Where only one of the first and second valve members 414a, 414b is deformable, the angular distance between the first and second valve members 414a, 414b may be configured such that an effective seal is formed between the first valve member 414a and the first right-diagonal seal portion 408a or the second left-diagonal seal portion 410b, and between the second valve member 414b and the second right-diagonal seal portion 408b or the first left-diagonal seal portion 410a over the range of anticipated deviations.

Specifically, where only the first valve member 414a is deformable, the deformation is able to counteract deviations which result in the distance between the first valve member 414a and the second valve member 414b being smaller than desired. Therefore, the spacing between the first valve member 414a and the second valve member 414b is set such that under the maximum anticipated deviation which results in the spacing being greater than desired, an effective seal is still formed between the first valve member 414a and the first right-diagonal seal portion 408a or the second left-diagonal seal portion 410b, and between the second valve member 414b and the second right-diagonal seal portion 408b or the first left-diagonal seal portion 410a.

Under the maximum anticipated deviation, the first valve member 414a may be subject to only minimal resistive force by the first right-diagonal seal portion 408a (in the first position) or the second left-diagonal seal portion 410b (in the second position) such that the second valve member 414a is substantially undeformed or only slightly deformed. Consequently, all other deviations from the desired spacing result in the first valve member 414a being deformed to a greater extent.

On the other hand, where only the second valve member 414b is deformable, the deformation is able to counteract deviations which result in the distance between the first valve member 414a and the second valve member 414b being greater than desired. Therefore, the spacing between the first valve member 414a and the second valve member 414b is set such that under the maximum anticipated deviation which results in the spacing being smaller than desired, an effective seal is still formed between the first valve member 414a and the first right-diagonal seal portion 408a or the second left-diagonal seal portion 410b, and between the second valve member 414b and the second right-diagonal seal portion 408b or the first left-diagonal seal portion 410a.

Under the maximum anticipated deviation, the second valve member 414b may be subject to only minimal resistive force by the second right-diagonal seal portion 408b (in the first position) or the first left-diagonal seal portion 410a (in the second position) such that the second valve member 414b is substantially undeformed or only slightly deformed. Consequently, all other deviations from the desired spacing result in the second valve member 414b being deformed to a greater extent.

There may also be deviations in the positions (or sizes) of the seal portions 408, 410. The deformation of the valve members 414a, 414b is again able to counteract these deviations so as to ensure that an effective seal is provided between the valve members 414a, 414b and the seal portions 408, 410. The deformation of the first valve member 414b is able to counteract deviations which result in the opposing surfaces of the first and second right-diagonal seal portions 408a, 408b and the opposing surfaces of the first and second left-diagonal seal portions 410a, 410b being respectively spaced further from one another than desired. Conversely, the deformation of the second valve member 414b is able to counteract deviations which result in the opposing surfaces of the first and second right-diagonal seal portions 408a, 408b and the opposing surfaces of the first and second left-diagonal seal portions 410a, 410b being respectively spaced closed to one another than desired.

As per the valve 302 of the fourth embodiment, the seal portions 408, 410 may also be deformable under force applied by the respective valve member. The combined deformation of the seal portions 408, 410 and the valve members 414a, 414b can counteract larger deviations in the positions of the seal portions 408, 410 and the valve members 414a, 414b.

As shown in FIGS. 17 and 18, the first and second valve members 414a, 414b may both be deformed when in the first and second positions. However, the first and second valve members 414a, 414b may be deformed to different extents in order to ensure proper sealing of both the first and second valve members 414a, 414b.

Although not shown, a bellows member similar to that described in the third embodiment may be implemented in the rotational valves 302, 402. Specifically, one or more of the left-diagonal seal portions 308, 408 and/or the right-diagonal seal portions 310, 410 may comprise a bellows member. The bellows member may be a single layer of material having a series of convolutions, each provided with a plurality of holes. The bellows member may be drawn across the end quadrant as the valve member moves between the first and second positions. Likewise, a stretchable material similar to that described previously may be implemented in the rotational valves 302, 402.

In the first, second and third embodiments, only two valve members may be used to achieve the same effect. Where only two valve members are used, these are located between the first upper seal portion and the first lower seal portion, and between the second upper seal portion and the second lower seal portion respectively. The positions of the seal portions may differ from those shown in order to accommodate the valve members on either side of ports B and D.

In the preceding embodiments, the deformation of the seal portions and/or the valve members is preferably elastic. Accordingly, the deformation provides a bias force which acts to return the valve element to the third position. However, some plastic deformation of the seal portions and the valve members may be acceptable in certain applications.

The stem and the valve members of the valve element have been described as being separate components, however they could, of course, be integrally formed.

In the four and fifth embodiments, the first and second seal portions of the right-diagonal and/or left-diagonal pair may be a single continuous or discontinuous seal. Nevertheless, the first and second seal portions are described as separate portions since the valve members seal against opposite surfaces of the seal portions.

Although the movable valve elements have been described as being actuated mechanically, it may also be possible to move the valve element using pneumatic or hydraulic actuation.

The inventive concepts described herein may be applied in valves having any number of ports and is not limited to the specific embodiments described and shown.

For example, the invention may be implemented in rotational valves having only two ports. Such a rotational valve may be formed by a tubular housing having a rotational valve element disposed therein. The valve element may have a first position in which the two ports are separated by the valve members and a second position where the valve members are aligned with the direction of fluid flow and thus allow fluid communication between the two ports.

Whilst the valve members and seal portions have been described as being deformed under the movement of the valve element, this need not be the case and the valve members and seal portions may be deformed by an external influence which deflects the seal portion and the respective valve member towards one another. For example, one or more of the valve members may be formed from a shape memory alloy which when heated deforms to a different shape (i.e., its original, cold-forged shape). Therefore, where the valve member does not seal with the seal portion, the valve member can be heated such that it deforms and causes the valve member to seal with the seal portion. A similar arrangement may be used to cause the seal portion to move towards the valve member. It should be appreciated that various other arrangements may be used to deform the valve members and seal portions.

Although the invention has been described with reference to a cough assist device CAD as shown in FIGS. 19 and 20, it will be appreciated that it may be applied in a much broader range of applications. In particular, the valves of the invention are well suited to applications which require high flow, but low pressure.

References to relative positions such as upper, lower, above, below, left, right should not be construed to indicate a specific orientation of the valve, and are simply provided for ease of reference.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention claimed is:

1. A valve comprising:
   a housing;
   a plurality of ports (A-E) disposed in the housing, said plurality of ports (A-E) comprising a first pair of ports (A, B) which are adjacent to one another and a second pair of ports (C, D) which are adjacent to one another;
   a movable valve element disposed within the housing, the valve element having a stem to which a first valve member and a second valve member are affixed;
   a first seal portion connected to the housing, the first seal portion being connected to the housing between the first pair of ports;
   a second seal portion connected to the housing, the second seal portion being connected to the housing between the second pair of ports;
   wherein a first distance between the first valve member and the second valve member is different from a second distance between the first seal portion and the second seal portion, wherein the first distance and the second distance are measured in a direction of movement of the valve element;
   wherein at least one of the first seal portion, the second seal portion, the first valve member, and the second valve member is deformable so as to counteract the difference between the first distance the second distance and allowing both (i) the first seal portion to be brought into a sealed configuration with the first valve member and, at the same time, (ii) the second seal portion to be brought into a sealed configuration with the second valve member, in order to seal the first pair of ports from one another and to seal the second pair of ports from one another at the same time.

2. A valve as claimed in claim 1, wherein the valve element has a first position in which the first and second seal portions are in the sealed configuration where the first pair of ports are sealed from one another with the first valve member and the second pair of ports are sealed from one another with the second valve member, and wherein the valve element has a second position in which the first and second seal portions are in an unsealed configuration where the first pair of ports are not sealed from one another with the first valve member and the second pair of ports are not sealed from one another with the second valve member.

3. A valve as claimed in claim 2, wherein the plurality of ports (A-E) comprises a first port (A), a second port (B), a third port (C), a fourth port (D) and a fifth port (E); the first pair of ports comprising the first and second ports (A, B) which are adjacent to one another, the second pair of ports comprising the third and fourth ports (C, D) which are adjacent to one another, a third pair of ports comprising the second and third ports (B, C) which are adjacent to one another and a fourth pair of ports comprising the fourth and fifth ports (D, E) which are adjacent to one another, and wherein the valve further comprises:

a third valve member affixed to the valve element;
a third seal portion connected to the housing and disposed between the third pair of ports;
a fourth seal portion connected to the housing and disposed between the fourth pair of ports;
wherein the first and second seal portions form a first pair of seal portions and the third and fourth seal portions form a second pair of seal portions, the first and second pairs of seal portions being offset such that the third seal portion is disposed between the first and second seal portions in the direction of movement of the valve element; and
wherein, in the second position of the valve, the third seal portion is in a sealed configuration with the second valve member and the fourth seal portion is in a sealed configuration with the third valve member, in order to seal the third pair of ports from one another and the fourth pair of ports from one another at the same time.

4. A valve as claimed in claim 2, wherein the plurality of ports comprise a first port (A), a second port (B), a third port (C) and a fourth port (D); the first pair of ports comprising the first and second ports (A, B), the second pair of ports comprising the third and fourth ports (C, D), a third pair of ports comprising the fourth and first ports (D, A) and a fourth pair of ports comprising the second and third ports (B, C), and wherein the valve further comprises:

a third seal portion connected to the housing and disposed between the third pair of ports;
a fourth seal portion connected to the housing and disposed between the fourth pair of ports; and
wherein, in the second position of the valve, the third seal portion is in a sealed configuration with the second valve member and the fourth seal portion is in a sealed configuration with the first valve member, in order to seal the third pair of ports from one another and the fourth pair of ports from one another at the same time.

5. A valve as claimed in claim 4, wherein the first port is configured to be connected to an atmosphere,
wherein the second port is configured to receive a first fluid pressure,
wherein the fourth port is configured to receive a second fluid pressure, and
wherein the third port is configured to provide an output for the valve;
wherein, when the valve element is in the first position, the second port is fluidically coupled to the third port; and
wherein, when the valve element is in the second position, the fourth port is fluidically coupled to the third port.

6. A valve as claimed in claim 5, wherein the first fluid pressure is a positive pressure and wherein the second fluid pressure is a negative pressure.

7. A valve as claimed in claim 5, wherein, when the valve element is in the first position, the fourth port is fluidically coupled to the first port; and wherein, when the valve element is in the second position, the second port is fluidically coupled to the first port.

8. A valve as claimed in claim 1, wherein the movable valve element is rotatable.

9. A valve as claimed in claim 1, wherein the movable valve element is linearly translatable.

10. A valve as claimed in claim 1, wherein some or all of the seal portions comprise a bellows member, the bellows member comprises one or more holes, wherein the one or more holes are obstructed when the bellows member is in a contracted state such that fluid communication across the bellows member is prevented, and wherein the one or more holes are unobstructed when the bellows member is in an expanded state such that fluid communication across the bellows member is permitted.

11. A valve as claimed in claim 1, wherein some or all of the seal portions comprise a stretchable material having one or more holes which increase in size as the stretchable material is stretched, such that the stretchable material prevents fluid communication through the stretchable material when unstretched and permits fluid communication through the stretchable material when stretched.

12. A cough assist device comprising a valve as claimed in claim 1.

13. A valve as claimed in claim 3, wherein the first port is configured to be connected to an atmosphere,
wherein the second port is configured to receive a first fluid pressure,
wherein the third port is configured to provide an output for the valve,
wherein the fourth port is configured to receive a second fluid pressure, and
wherein the fifth port is configured to be connected to the atmosphere;
wherein, when the valve element is in the first position, the second port is fluidically coupled to the third port; and
wherein, when the valve element is in the second position, the fourth port is fluidically coupled to the third port.

14. A valve as claimed in claim 13, wherein the first fluid pressure is a positive pressure and wherein the second fluid pressure is a negative pressure.

15. A valve as claimed in claim 14, wherein, when the valve element is in the first position, the fourth port is fluidically coupled to the fifth port; and wherein, when the valve element is in the second position, the second port is fluidically coupled to the first port.

* * * * *